(12) United States Patent
Horkay et al.

(10) Patent No.: US 10,078,124 B2
(45) Date of Patent: *Sep. 18, 2018

(54) PHANTOM FOR DIFFUSION MRI IMAGING

(71) Applicant: The United States of America, as represented by the Secretary, Dept. of Health and Human Services, Washington, DC (US)

(72) Inventors: Ferenc Horkay, Rockville, MD (US); Carlo Pierpaoli, Rockville, MD (US); Peter J. Basser, Washington, DC (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 13 days.

This patent is subject to a terminal disclaimer.

(21) Appl. No.: 15/448,760

(22) Filed: Mar. 3, 2017

(65) Prior Publication Data

US 2017/0242090 A1  Aug. 24, 2017

Related U.S. Application Data

(63) Continuation of application No. 13/146,058, filed as application No. PCT/US2010/022088 on Jan. 26, 2010, now Pat. No. 9,603,546.

(60) Provisional application No. 61/147,314, filed on Jan. 26, 2009.

(51) Int. Cl.
  *G01R 33/58* (2006.01)
  *A61B 5/055* (2006.01)
  *G01R 33/563* (2006.01)

(52) U.S. Cl.
  CPC .............. *G01R 33/58* (2013.01); *A61B 5/055* (2013.01); *G01R 33/56341* (2013.01)

(58) Field of Classification Search
  USPC .......................... 324/300–322; 600/407–435; 382/128–131
  See application file for complete search history.

(56) References Cited

U.S. PATENT DOCUMENTS

| | | | |
|---|---|---|---|
| 5,312,755 | A | 5/1994 | Madsen |
| 5,545,995 | A | 8/1996 | Schneider et al. |
| 5,633,584 | A | 5/1997 | Maryanskl |
| 6,675,035 | B1 | 1/2004 | Grable |
| 6,791,327 | B2 | 9/2004 | Skloss |
| 7,612,560 | B2 | 11/2009 | Wiggins |
| 8,134,363 | B2 | 3/2012 | Yanasak |

(Continued)

*Primary Examiner* — Melissa Koval
*Assistant Examiner* — Tiffany Fetzner
(74) *Attorney, Agent, or Firm* — Polsinelli PC; Ron Galant

(57) ABSTRACT

A phantom calibration body (12) for calibrating diffusion MRI device (16) that mimics a material such as a mammalian tissue is disclosed. The phantom calibration body (12) includes a homogeneous aqueous solution (30) that contains a mixture of low molecular-weight and high molecular-weight polymers housed in a container (14) that is placed in the diffusion MRI device (16) for obtaining one or more diffusion MRI images of the phantom calibration body (12). A measure of diffusivity is calculated for each of the one or more diffusion MRI images in order to calibrate the diffusion MRI device. Methods of using the phantom calibration body (12) to calibrate diffusion MRI device (16) are also disclosed.

19 Claims, 9 Drawing Sheets

(56) References Cited

U.S. PATENT DOCUMENTS

| | | | |
|---|---|---|---|
| 9,603,546 B2* | 3/2017 | Horkay | A61B 5/055 |
| 2004/0119474 A1 | 6/2004 | Skloss | |
| 2006/0269479 A1 | 11/2006 | Colton | |
| 2008/0265882 A1 | 10/2008 | Wiggins | |
| 2008/0269594 A1 | 10/2008 | Rainer et al. | |
| 2009/0058417 A1 | 3/2009 | Yanasak | |
| 2012/0068699 A1* | 3/2012 | Horkay | A61B 5/055 |
| | | | 324/300 |
| 2017/0242090 A1* | 8/2017 | Horkay | G01R 33/58 |

* cited by examiner

PHANTOM FOR DIFFUSION MRI IMAGING

FIELD

This document relates to a phantom calibration body and methods of using the phantom calibration body to calibrate diffusion MRI imaging devices. The phantom calibration body that includes a homogeneous aqueous solution that contains a mixture of low molecular-weight and high molecular-weight polymers formulated to provide a specified water diffusivity and viscosity.

BACKGROUND

Diffusion magnetic resonance imaging (diffusion MRI) combines nuclear magnetic resonance (NMR) imaging principles with those that encode molecular diffusion in the NMR signal by magnetic field gradient pulses. Molecular diffusion refers to the random translational motion of molecules, also called Brownian motion that results from the thermal energy carried by these molecules. The rationale for diffusion MRI is that during the random and diffusion driven displacements, these molecules probe tissue structure at a microscopic scale well beyond the usual image resolution available in other imaging technologies.

Water is the most convenient molecular species to study using diffusion MRI, although other metabolites may also be studied. During typical diffusion times of about 50 msec, water molecules may move in tissue, such as brain tissue, over distances of about 10 μm while bouncing, crossing, or interacting with many other tissue components, such as cell membranes, fibers, or macromolecules. For example, the overall effect observed in a diffusion MRI image voxel of several $mm^3$ reflects on a statistical basis the displacement distribution of the water molecules present within this particular diffusion MRI image voxel. The observation and analysis of this displacement distribution may provide unique insights into the structure and geometric organization of tissues.

Diffusion, as governed by Fick's law, may be expressed as:

$$J = -D\nabla(C) \quad (1)$$

wherein C is the concentration, D is the diffusivity, and J is the flux vector.

Diffusion MRI characterizes the diffusion coefficient, D, by experimental measurements. In particular, diffusion MRI makes use of the attenuation of the diffusion MRI signal due to the diffusion and resulting random movement of water molecules over time. For a single diffusion MRI image, this attenuation, A, may be expressed as:

$$A = e^{-(bD)} \quad (2)$$

wherein b, or the "b-value", is a numerical quantity used to characterize the timing, amplitude, and shape of magnetic gradients pulses used in the diffusion MRI acquisition sequence.

In biological tissues water diffusion may be an anisotropic process, where the b-value and the diffusion coefficient D may be characterized as tensors and the diffusivity of water molecules may be captured using tensor characterizations. However, for many purposes, apparent diffusion coefficient (ADC), which is a single scalar quantity, may be used to capture the value of water diffusivity within a given sample along a particular direction.

The ADC may be calculated by acquiring two or more diffusion MRI images using different magnetic field gradient durations or amplitudes, thereby resulting in different b-values for each diffusion MRI image derived using equation (2). The contrast in an ADC map derived from a comparison of two or more diffusion MRI images depends on the spatially distributed diffusion coefficients of the acquired tissues and excludes effects from $T_1$ or $T_2^*$ relaxations. By acquiring multiple diffusion MRI images with different b-values, and then plotting the logarithm of signal intensity as a function of these b-values, the ADC may be determined from the slope of the acquired plotted data.

Diffusion MRI has been applied clinically to detect brain ischemia, following the discovery in a cat brain model that water diffusion drops at a very early stage of an ischemic event. The increased sensitivity of diffusion-weighted diffusion MRI in detecting acute ischemia is due to the restricted intracellular motion of water protons in a manner similar to cytotoxic edema. A decreased ADC, as measured by a diffusion MRI device, is a sensitive indicator of early brain ischemia that has gained widespread acceptance. By detecting changes in water diffusivity, diffusion MRI may provide patients with the opportunity to receive suitable treatment at a stage when brain tissue might still be salvageable.

In order to develop and implement clinical diagnostic criteria that incorporate diffusion MRI measurements, the diffusion MRI data must be obtained in a precise, accurate and repeatable manner. However, the diffusion MRI data may vary between different diffusion MRI devices, or the data may vary for the same diffusion MRI device over time due to gradual changes in the hardware of the diffusion MRI device or updates in data acquisition software used by the diffusion MRI device to process the acquired data. In order to achieve a suitable level of precision and accuracy, periodic calibration of the diffusion MRI device is essential.

It is known that diffusion MRI devices may employ a phantom calibration body to calibrate these types of devices. Existing phantom calibration bodies have been constructed from gels and polymer materials to calibrate various aspects of the diffusion MRI device; however, none of these existing phantom bodies are stable, non-flammable, non-toxic, transportable, vibration dampening, and/or exhibit isotropic diffusion properties within a range of viscosities. In addition, common additives, including contrast agents such as magnesium chloride and gadolinium-diethylenetriamine pentaacetic acid (Gd-DTPA) have been incorporated into the materials of existing phantom calibration bodies. However, these additives failed to alter the diffusion properties sufficiently to mimic the diffusivity of tissues suitable for calibrating a diffusion MRI device.

As such, there exists a need in the art for a phantom calibration body with known and controllable water diffusivity characteristics that mimic those in the tissues to be subjected to diffusion MRI. Further, there exists a need for a method of making a phantom calibration body in which the water diffusivity may be adjusted to match the diffusivity of the particular tissues to be subjected to diffusion MRI. There also exists a need in the art for a method of calibrating a diffusion MRI device for diffusion and image resolution characteristics using the phantom calibration body.

SUMMARY

The present invention may be a method for calibrating a diffusion MRI device includes providing a phantom calibration body having a homogenous aqueous solution including a first polymer having a high molecular-weight and a second polymer having a low molecular-weight. The homogenous aqueous solution has a diffusivity that is essentially the same as a target material and a viscosity ranging from about $10^2$ cSt to about $10^6$ cSt. The method further includes placing the phantom calibration body in a diffusion MRI device and obtaining diffusion imaging data of the phantom calibration body by scanning the phantom calibration body with the diffusion MRI device. The method then calculates a diffusivity measurement that is indicative of water diffusivity of the homogeneous aqueous solution.

The present invention may be a method of manufacturing a phantom calibration body having a homogeneous aqueous solution includes combining a high molecular-weight polymer and water to produce a first solution and then combining a low molecular-weight polymer and water to produce a second solution with a high molecular-weight polymer. The method then includes mixing the first solution and the second solution to form a homogeneous aqueous solution having a diffusivity that is essentially the same as a target material and a viscosity ranging from about $10^3$ cSt to about $10^6$ cSt.

The present invention may be a system for calibrating an imaging device includes a phantom calibration body having a homogeneous aqueous solution including a first polymer having a high molecular-weight and a second polymer having a low molecular-weight. The homogenous aqueous solution has a diffusivity that is essentially the same as a target material and a viscosity ranging from about $10^3$ cSt to about $10^6$ cSt. The system further includes a diffusion MRI device for acquiring one or more diffusion MRI images with each of the one or more diffusion MRI images having a diffusion property.

The present invention may be a computer-readable media is encoded with a diffusion MRI calibration system for calibrating a diffusion MRI device using a phantom calibration body. The computer-readable media includes computer-readable instructions executable by at least one processor for performing the steps of obtaining one or more diffusion MRI images of the phantom calibration body using the diffusion MRI device. The phantom calibration body includes a homogeneous aqueous solution having a first polymer including a high molecular-weight and a second polymer with a low molecular-weight. The homogenous aqueous solution has a diffusivity that is essentially the same as a target material and a viscosity ranging from about $10^3$ cSt to about $10^6$ cSt. The computer-readable instructions further include making diffusivity measurements for each of the one or more diffusion MRI images of the phantom calibration body using at least one processor and then calibrating the diffusion MRI device based on the diffusivity measurements calculated for each of the plurality of diffusion MRI images of the phantom calibration body.

The present invention may be a method for calibrating a diffusion MRI device includes providing an isotropic phantom calibration body having a homogenous aqueous solution including a first polymer having a high molecular-weight and a second polymer having a low molecular-weight. The homogenous aqueous solution has a diffusivity that is essentially the same as a target material and a viscosity ranging from about $10^2$ cSt to about $10^6$ cSt. The method further includes placing the phantom calibration body in a diffusion MRI device and obtaining diffusion imaging data of the phantom calibration body by scanning the phantom calibration body with the diffusion MRI device. The method then determines the presence or absence of an artifactual orientational systematic bias in the diffusion imaging data of the isotropic phantom calibration body.

Additional objectives, advantages and novel features will be set forth in the description which follows or will become apparent to those skilled in the art upon the examination of the drawings and detailed description which follows. Combinations and subcombinations of the systems and methods described herein may be made.

BRIEF DESCRIPTION OF THE DRAWINGS

The following figures illustrate various aspects of the embodiments described herein.

Corresponding reference characters indicate corresponding elements among the view of the drawings. The headings used in the figures should not be interpreted to limit the scope of the claims.

DETAILED DESCRIPTION

Figure 1:
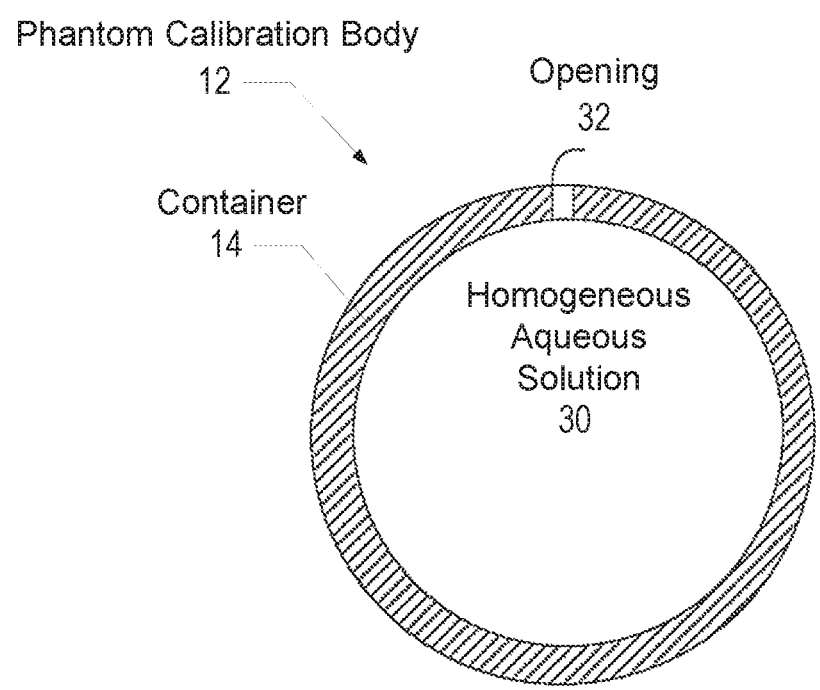
FIG. 1 is a cross-sectional view illustrating an embodiment of a spherical phantom calibration body.

Provided herein is a phantom calibration body for the calibration of a diffusion MRI device, and methods of making and using the phantom calibration body. As will be discussed below, the phantom calibration body may include an aqueous solution of a high molecular-weight polymer and a low molecular-weight polymer contained within a container. The materials of the phantom calibration body may be selected to be non-toxic, non-flammable, homogeneous, and possess stable diffusion properties over repeated calibrations and extended periods of storage. In addition, the materials of the phantom calibration body are selected to achieve critical performance characteristics such as a desired diffusivity of water and a desired viscosity within the aqueous solution.

The phantom calibration body may be designed to have a diffusivity value that is similar to the diffusivity of water in a variety of living and/or non-living materials on which diffusion MRI imaging is to be performed, such as in vivo human tissues. The viscosity of the aqueous solution of the phantom calibration body may have any value within a broad range. The viscosity is selected in order to minimize the confounding effects on the diffusion MRI measurements caused by vibration of the phantom calibration body. The vibrations may be attributed to various sources such as vibration of the diffusion MRI device itself as well as vibrations from the surrounding environment that can vibrate the diffusion MRI device. The particular diffusivity and viscosity characteristics of the phantom calibration body may be selected based on factors such as the particular material to be measured in the diffusion MRI device, the performance characteristics of the diffusion MRI device to be calibrated, and the particular purpose of the calibration. The phantom calibration body may be used to calibrate a diffusion MRI device in a variety of different contexts, such as routine maintenance of diffusion MRI devices in institutional diffusion MRI or radiology departments, quality assurance and/or quality control processes by diffusion MRI device vendors during installation or repair, and diffusion MRI device manufacturing or development processes. In addition, because the container is of known size and dimensions, the phantom calibration body may also function as a resolution phantom for calibrating the MRI device.

A detailed description of the phantom calibration body, methods of making the phantom calibration body and methods of using the phantom calibration body are presented below. Other aspects of the invention will become apparent to the skilled artisan by the following description of the invention.

1. Definitions

Before the present materials and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise. For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6, 9, and 7.0 are explicitly contemplated.

a. Polymers

As used herein, the term "polymer" refers to any molecule composed of repeating monomer structural units, such as, homopolymers, copolymers, heteropolymers, branched polymers, star copolymers, brush copolymers, comb copolymers, graft copolymers, and block copolymers.

b. Diffusion MRI

As used herein, the term "diffusion MRI" refers to any post-processing methodology that extracts information from one or more diffusion-weighted images, such as diffusion imaging or diffusion tensor imaging methods. In diffusion-weighted imaging (DWI), each image voxel (i.e., three-dimensional pixel) has an image intensity that reflects the rate of water diffusion at that location. Diffusion tensor imaging (DTI) scans derive information from the data using 3D or multidimensional vector algorithms based on three, six, or more gradient directions, sufficient to compute the diffusion tensor.

c. Diffusion-Weighted Image

As used herein, the term "diffusion-weighted image" refers to any diffusion MRI image in which the signal intensity of each voxel is influenced by the diffusivity of the object image.

d. Low Molecular Weight

As used herein, the term "low molecular weight" refers to any polymer having a molecular weight between about 5 kDa and about 40 kDa.

e. High Molecular Weight

As used herein, the term "high molecular weight polymer" refers to any polymer having a molecular weight between about 40 kDa and about 1000 kDa.

e. Resolution Phantom

As used herein, the term "resolution phantom" refers to any phantom body of known dimensions that may serve as a benchmark to calibrate various aspects of the spatial resolution of the diffusion MRI image, such as image distortion.

f. Mixing Ratio

As used herein, the term "mixing ratio" is defined herein is the ratio of the weight of high molecular weight polymers to the weight of low molecular-weight polymers included in an aqueous solution.

g. Tensor

As used herein, the term "tensor" refers to geometric entities introduced into physics to extend the notion of scalars, vectors, and matrices.

h. Solution

As used herein, the term "solution" refers to a homogeneous mixture composed of two or more substances that may include a suspension or an emulsion.

i. Polydispersity Index

As used herein, the term polydispersity index (PDI) refers to a measurement of the distribution of molecular mass in a given polymer sample and is calculated by the weight average molecular weight divided by the number average molecular weight. It further refers to the distribution of individual molecular masses in a batch of polymers and is denoted by the formula PDI=Mw/Mn.

2. Phantom Calibration Body

Referring to the drawings, an embodiment of a phantom calibration body is illustrated and generally indicated as 12 in FIG. 1. The phantom calibration body 12 includes a homogeneous aqueous solution 30 having a mixture of a high molecular weight polymer and a low molecular weight polymer. The homogeneous aqueous solution 30 is contained within a volume defined by the walls of a container 14. The walls of the container 14 may further define an opening 32 that functions as a conduit through which the volume of the container 14 may be filled with the aqueous solution 30.

a. Homogeneous Aqueous Solution

The homogeneous aqueous solution 30 is formulated to provide a volume with known dimensions that has an essentially spatially uniform diffusivity of water throughout the volume. The diffusivity of water within the solution 30 may be controlled to any value within a range of desired values that typically correspond to a diffusivity value near that of a material to be measured by the diffusion MRI device by varying the combined concentration of low and high molecular weight polymers in the solution 30.

The composition of the homogeneous aqueous solution 30 may further incorporate other additives including, but not limited to, antibacterial agents, ionic and non-ionic surfactants, DMSO, $T_1$ contrast agents, $T_2^*$ contrast agents, and $D_2O$ in order to impart additional desirable properties to the solution 30 such as resistance to microbial degradation, enhanced contrast of diffusion MRI images, and enhanced solubility of the polymers in the solution 30, and $T_1$ and $T_2^*$ relaxivity characteristics that mimic the materials to be measured in the diffusion MRI device. The materials of the homogeneous aqueous solution 30 are further selected to possess other properties such as non-toxicity, non-flammability, and the ability to maintain a stable diffusivity of water over extended periods of storage and use. In particular, the materials included in the homogeneous aqueous solution 30 may be selected to minimize the evaporation of water from the solution 30, any associated film formation or precipitation, and to inhibit the formation of aggregations of compounds that would degrade the homogeneity of the solution 30. The materials of the homogeneous aqueous solution 30 also inhibit the formation of bubbles within the solution 30.

Another critical feature of the homogeneous aqueous solution 30 is viscosity. The viscosity of the homogeneous aqueous solution 30 may be controlled to any value within a range of desired values by varying the amount of low molecular weight polymer in the solution relative to the amount of high molecular weight polymer in the composition of the solution 30. The viscosity of the homogeneous aqueous solution 30 may dampen the effects of external vibrations associated with the diffusion MRI device and surrounding environment during calibration of an MRI device 16 (FIG. 2) thereby resulting in reduced measurement artifacts.

A detailed description of the materials forming the homogeneous aqueous solution 30 and the influence of the choice of materials included in the homogeneous aqueous solution 30 on the characteristics of the solution 30 including water diffusivity and viscosity, are presented below.

i. Low Molecular Weight and High Molecular Weight Polymers

The particular compound and compounds selected for the low molecular weight polymers and high molecular weight polymers, and the amount of each type of polymer included in the solution 30 largely determine the critical characteristics of the solution 30 such as water diffusivity, viscosity, homogeneity, and stability over time.

1. Combined Polymer Concentration Governs Diffusivity of Solution

The diffusivity of water within the homogeneous aqueous solution 30 is governed essentially by the combined concentration of the high molecular weight polymer and the low molecular weight polymer within the solution 30. The diffusivity of water may also be governed by the temperature of the homogeneous aqueous solution 30. In addition, the diffusivity of water within the homogeneous aqueous solution 30 is relatively insensitive to the individual molecular weights of each polymer in the solution 30. The homogeneous aqueous solution 30 may be designed to have any diffusivity value within a relatively broad range. The diffusivity of the homogeneous aqueous solution 30 may range from about $2\times10^{-4}$ mm$^2$/s to about $3\times10^{-3}$ mm$^2$/s. Alternatively, the diffusivity of the homogeneous aqueous solution 30 may range from about $2\times10^{-4}$ mm$^2$/s to about $4\times10^{-4}$ mm$^2$/s, from about $3\times10^{-4}$ mm$^2$/s to about $5\times10^{-4}$ mm$^2$/s, from about $4\times10^{-4}$ mm$^2$/s to about $6\times10^{-4}$ mm$^2$/s, from about $5\times10^{-4}$ mm$^2$/s to about $7\times10^{-4}$ mm$^2$/s, from about $6\times10^{-4}$ mm$^2$/s to about $8\times10^{-4}$ mm$^2$/s, from about $9\times10^{-4}$ mm$^2$/s to about $1.1\times10^{-3}$ mm$^2$/s, from about $1\times10^{-3}$ mm$^2$/s to about $2\times10^{-3}$ mm$^2$/s, from about $1.5\times10^{-3}$ mm$^2$/s to about $2.5\times10^{-3}$ mm$^2$/s, or from about $2\times10$ mm$^{-2}$/s to about $3\times10^{-3}$ mm$^2$/s.

The homogeneous aqueous solution 30 may incorporate a concentration of polymers selected to achieve a water diffusivity that is essentially matched to the diffusivity of a material to be measured using diffusion MRI. In particular, the homogeneous aqueous solution 30 may be designed to have a diffusivity value that is similar to the diffusivity of water in a variety of living and/or non-living materials on which diffusion MRI is to be performed, such as mammalian tissues. Non-limiting examples of mammalian tissues may include brain tissue, liver tissue, prostate tissue, breast tissue, cardiac tissue, pancreatic tissue, and kidney tissue. Because the homogeneous aqueous solution 30 used to manufacture the phantom calibration body 12 has a reproducible behavior and a known dependence of diffusivity on polymer concentration, the phantom calibration body 12 may be used to mimic diffusion properties of tissues other than brain tissue. Such an application has particular importance in organ or whole body imaging such as screening, assessing or diagnosing cancer. Exemplary tissues may include skeletal, cardiac or smooth muscle, cartilage, and other extracellular matrix based tissue. Organs whose tissue could also be mimicked with the phantom calibration body 12 may include the liver, kidney, prostate, testicles and other reproductive organs, stomach, heart, lymph nodes, tongue and other bodily organs.

In addition, because the homogeneous aqueous solution 30 used to manufacture the phantom calibration body 12 has a reproducible behavior and a known dependence of diffusivity on polymer concentration, the phantom calibration body 12 may be also be used to mimic diffusion properties in other biological and non-biological media. For example, the biological media may include agricultural products including vegetables, fruits, meats, and dairy products, such as cheeses, yogurt, and milk products. Other biological media may include processed foods, such as candy, chocolate, jams and jelly, peanut butter and other nut-based butters, beverages including sodas, syrups, juices, and oils such as canola, olive, peanut and other nut-based oils. Other potential applications for the phantom calibration body 12 may include calibration of MRI-based experiments to test, monitor, assess or evaluate aquatic animals for sale, such as fish, scallops, clams, oysters and other aquatic specimens.

The homogeneous aqueous solution 30 may include low molecular weight and high molecular weight polymers in a combined amount of at least 0.1% (w/w). The homogeneous aqueous solution 30 may include low molecular weight and high molecular weight polymers in a combined amount ranging from about 0.1% to about 1.0%, 1.0% to about 5% (w/w), 5% to about 20% (w/w), 20% to about 30% (w/w), from about 25% to about 35% (w/w), from about 30% to about 40% (w/w), from about 35% to about 45% (w/w), from about 40% to about 50% (w/w), from about 45% to about 55% (w/w), from about 50% to about 60% (w/w), from about 55% to about 65% (w/w), from about 60% to about 70% (w/w), from about 65% to about 75% (w/w), and from about 70% to about 80% (w/w).

The polymers that may be included in the homogenous solution may be selected based upon its conformational and polydispersity index. The PDI of polymers that may be used in the solution may have a PDI value of 1 to 20, or 1, 2, 3, 4, 5, 6, 7, 8, 9, 10, 11, 12, 13, 14, 15, 16, 17, 18, 19, or 20 thereof.

2. Mixing Ratio Governs the Viscosity of Solution

The viscosity of the homogeneous aqueous solution 30 may be used to minimize the effect of convection within the solution 30 that may introduce artifacts into the water diffusion properties of the phantom calibration body 12. Undesirable convective cells or eddies may form within the homogeneous aqueous solution 30 of the phantom calibration body 12 due to movement of technicians near the diffusion MRI device 16, movements of mechanical elements within the diffusion MRI device, or ambient vibrations and vibrations created by the diffusion MRI device or associated equipment. The viscosity of the aqueous solution 30 may exert damping shear stresses that tend to minimize the propagation of any convective or advective motion that may form within the phantom calibration body 12 during its use in the diffusion MRI device 16.

The viscosity of the homogeneous aqueous solution 30 may have any value within a broad range. The viscosity of the homogeneous aqueous solution 30 may range from about 10 cSt to about 10,000,000 cSt. Alternatively, the viscosity of the aqueous solution 30 may range from about 10 cSt to about 1000 cSt, from about 100 cSt to about 10,000 cSt, from about 1000 cSt to about 100,000 cSt, from about 50,000 cSt to about 250,000 cSt, from about 100,000 cSt to about 300,000 cSt, from about 200,000 cSt to about 400,000 cSt, from about 300,000 cSt to about 500,000 cSt, from about 400,000 cSt to about 600,000 cSt, from about 500,000 cSt to about 700,000 cSt, from about 600,000 cSt to about 800,000 cSt, from about 700,000 cSt to about 900,000 cSt, and from about 800,000 cSt to about 1,000,000 cSt. In an exemplary embodiment, the viscosity of the aqueous solution 30 may be about 100,000 cSt. The particular viscosity of the homogeneous aqueous solution 30 may be selected to be sufficiently high in order to damp out the effects of vibrations, without adversely affecting other aspects of the solution 30, such as the ability to eliminate air bubbles that may form within the solution 30 during manufacture, use or storage and the ease with which the solution 30 may be inserted into the container 14 during the manufacture of the phantom calibration body 12. The addition of a surfactant to the homogeneous aqueous solution 30 may render the solution easier to transfer into the container 14.

The relative amounts of low and high molecular weight polymers may be quantified using a mixing ratio, defined herein as the ratio of the weight of the high molecular weight polymer to the weight of the low molecular-weight polymer included in the homogeneous aqueous solution 30. The mixing ratio may range from about 1:100 to about 100:1. Alternatively, the mixing ratio may range from about 1:100 to about 1:10, from about 1:50 to about 1:5, from about 1:10 to about 1:1, from about 1:5 to about 10:1, or from about 5:1 to about 100:1. In an exemplary embodiment, the mixing ratio of high molecular-weight polymer to low molecular-weight polymer is about 9 to 1. The upper limit of the mixing ratio may be constrained by the solubility of the polymers at the intended concentration of the mixture.

In general, the polymers included in the homogeneous aqueous solution 30 may be selected from at least two or more groups of polymers having different ranges of molecular weights. The range of molecular weight of one polymer group may overlap with the weight range of one or more of the other polymer groups, or each of weight ranges of the polymer groups may be distinct from each of the other polymer groups. For example, the homogeneous aqueous solution 30 may include three polymer groups: a low molecular weight group, an intermediate molecular weight group, and a high molecular weight group. Alternatively, the molecular weights of the polymers included in the homogeneous aqueous solution 30 may have an essentially continuous distribution of molecular weights, and one or more statistical descriptions of the distribution such as a mean, a median, a mode, an average, or a standard deviation may be used to select a particular distribution of polymer molecular weights in order to obtain the desired qualities of the homogeneous aqueous solution 30.

In general, the viscosity of a polymer solution increases significantly with the molecular weight of the polymers included in that solution. In addition to increasing the viscosity of the homogeneous aqueous solution 30, high molecular-weight polymers tend to generate more consistent NMR signals, while the low molecular-weight polymers generate more noisy NMR signals due to the relatively higher proportion of end-groups in the low molecular-weight polymers.

The low molecular-weight polymer may have a molecular weight from about 5 kDa to about 40 kDa, while that of a high molecular-weight polymer may have a molecular weight from about 40 kDa to about 1000 kDa. The low molecular-weight polymer may alternatively have a molecular weight from about 5 kDa to about 15 kDa, from about 10 kDa to about 20 kDa, from about 15 kDa to about 25 kDa, from about 20 kDa to about 30 kDa, from about 25 kDa to about 35 kDa, or from about 30 kDa to about 40 kDa. The high molecular-weight polymer may alternatively have a molecular weight from about 40 kDa to about 1000 kDa, from about 100 kDa to about 300 kDa, from about 200 kDa to about 400 kDa, from about 500 kDa to about 700 kDa, from about 600 kDa to about 800 kDa, from about 700 kDa to about 900 kDa, or from about 800 kDa to about 1000 kDa.

The high molecular-weight polymer may have a molecular weight of at least about twice that of the low molecular-weight polymer, at least about three times that of the low molecular-weight component, at least about four times that of the low molecular-weight component, or at least about five times that of the low molecular-weight component. The degree of molecular weight range overlap for the low molecular weight and high molecular weight polymers may depend on the particular choice of the molecular weight for the low molecular-weight polymer. The high molecular-weight polymer may have a molecular weight of at least about four times that of the low molecular-weight polymer. For example, for a low molecular-weight polymer having a molecular weight of 10 kDa, the high molecular-weight polymer may have a molecular weight of only 40 kDa.

As will be appreciated by persons in the art, the ratio and total concentration of the low and high molecular-weight polymers may be selected to achieve desired levels of transport properties such as viscosity, convection, and diffusion of the homogeneous aqueous solution 30.

3. Choice of Polymer Compound Influences Stability of Solution

In order to achieve a diffusivity of water in a homogeneous aqueous solution 30 in a phantom calibration body 12 that mimics materials such as biological mammalian tissues, a relatively high concentration of solutes may be necessary. The selection of solute materials for the homogeneous aqueous solution 30 is constrained by a number of physical factors. A high concentration of a small molecule solute in the homogeneous aqueous solution 30 is known to be vulnerable to undesirable crystallization and/or formation of metaphasic structures when a threshold of concentration of the small molecule solute is exceeded, when a certain temperature is reached, or when a small impurity core develops in the homogeneous aqueous solution 30.

Short-chain low molecular-weight polymer materials are subject to similar constraints that may impose an upper limit on the concentration of the polymer in the homogeneous aqueous solution 30. For example, large concentrations of cellulose solution or cellulose derivatives may lead to crystal formation in a homogeneous aqueous solution 30 with resulting ordered structures that degrade the homogeneity of the solution 30. Although the use of long-chain high molecular-weight polymers in the homogeneous aqueous solution 30 may result in a solution that is resistant to crystallization at high solute concentrations, the viscosity of the solution 30 may be unacceptably high for practical applications, such as calibration of a diffusion MRI device 16.

It has been surprisingly found that a homogeneous aqueous solution 30 including a mixture of both short-chain low molecular-weight and long-chain high molecular-weight polymer materials achieves solute concentrations that are sufficiently high in order to mimic the diffusivity of materials such as mammalian tissues, while minimizing the risk of crystallization and avoiding excessively high solution viscosity. The low molecular-weight and long-chain high molecular-weight polymers may be selected to be different polymer species. In order to minimize phase separation that may degrade the homogeneity of the homogeneous aqueous solution 30, the low molecular-weight and high molecular-weight polymers may be essentially the same polymer species. In addition to influencing the viscosity of the homogeneous aqueous solution 30 as discussed above, the inclusion of a low molecular weight polymer may further enhance the solubility of the high molecular weight polymer in the aqueous solution 30.

In addition to the physical constraints influencing the selection of solutes to be included in the homogeneous aqueous solution 30, the chemical properties of the solutes also may influence the selection of solutes. Polymers that tend not to associate or form hydrogen bonds or form extended clusters in concentrated homogeneous aqueous solutions and tend not to exhibit aging effects such as spontaneous polymer cross-linking, cleavage, or other degradation are excellent candidate polymers for use in the homogeneous aqueous solution 30 of the phantom calibration body 12.

Polymers suitable for use in the phantom calibration body 12 may include, but are not limited to, water soluble and water dispersible polymers such as polyvinyl alcohol, polysaccharides, cellulose and its derivatives, polyvinyl pyrrolidone, polyacrylamides, polyacrylates, and polyethylene glycols. Other non-limiting examples of suitable polymers include copolymers such as copolymers of statistical type (not typically block type) and may contain polar groups. Non-limiting examples of comonomers include acrylic acid, methacrylic acid, acrylamide, vinyl pyrrolidone, vinyl alcohol, and small vinyl monomers. In an exemplary embodiment, the copolymer may include from about 80% to 100% vinyl pyrrolidone and from 0% to about 20% comonomer or dimethylsiloxane-ethylene oxide copolymers. The phantom calibration body 12 may include mixtures of polymers, mixtures of copolymers, and mixtures of polymers and copolymers. As used herein, polymers and copolymers encompass these mixtures as well. In an exemplary embodiment, the polymer included in the homogeneous aqueous solution 30 is polyvinyl pyrrolidone.

The phantom calibration body 12 may include materials that impart a magnetic resonance signal. For example, the homogeneous aqueous solution 30 of the phantom calibration body 12 may include signal bearing substances including, but not limited to, aqueous paramagnetic solutions, pure gels of gelatin, agar, polyvinyl alcohol, water soluble silicone compounds, polyacrylamide, agarose, organic doped gels, gels doped with paramagnetic additives, and reverse micelle solutions. The measured diffusivity of the phantom calibration body 12 may be independent of the diffusion time, indicating a Gaussian diffusion of a single population of spins.

The polymers included in the homogeneous aqueous solution 30 may be obtained commercially in the desired molecular weight ranges. Alternatively, the polymers may be obtained at a range of molecular weights and separated into molecular weight groups using techniques known in the art such as serial filtration and sifting. The polymers may be synthesized and then fractionated to the desired one or more molecular weights using techniques known in the art.

The phantom calibration body 12 may further contain a plurality of fibers of additional materials such as silks, cloth tapes, wood, and glass fibers soaked in the aqueous solution 30.

b. Container

The homogeneous aqueous solution 30 used for the phantom calibration body 12 is housed within a container 14 constructed of a material that is essentially transparent to the diffusion MRI device 16 during calibration of the MRI device 16. Non-limiting examples of materials suitable for the construction of the container include plastic, composites, or other diffusion MRI-compatible materials. The container 14 may include an array of plastic containers, such as polycarbonate, polyethylene, polystyrene, polyvinvyl chloride, or polytetrafluoroethylene bottles, or glass bottles, each containing varying concentrations of homogeneous aqueous solutions 30. In an exemplary embodiment, the material of the container is plastic.

A spherical container 14 may minimize suscepti9biloity effects relative to other container shapes. Alternatively, the container may be an anthropogenic container. The shape of the container 14 may be selected to minimize susceptibility effects resulting from NMR signal distortions at the interface of the container wall and the aqueous solution 30. In an exemplary embodiment, the shape of the container is spherical.

Without being bound to any particular theory, a spherical container may minimize susceptibility effects relative to other container shapes. When placed in a parallel magnetic field, the magnetic field is minimally distorted by the spherical container wall. Thus, any variations in the measured response to the applied magnetic field are more likely to be due to non-homogeneity of the applied magnetic field, rather than artifacts in the measurements related to spurious susceptibility effects.

The shape of the container 14 may be selected to be an easily measured shape such as a cube, a rectangular prism, or a cylinder. In this case, because the container 14 is of known size, the size of a diffusion MRI image of the container 14 may be used to calibrate the image distortion of the diffusion MRI image by the diffusion MRI device 16. In this manner, the phantom calibration body 12 may function as a distortion phantom as well as a diffusion phantom.

The homogeneous aqueous solution 30 may replace a nickel chloride or copper sulfate solution used in an existing resolution phantom, such as a General Electric (GE) Healthcare resolution phantom accompanying a GE MR scanner. The additional sulfate additive may be included to keep the polymer solution sterile. The aqueous solution 30 may be inserted into a commercially available anatomy phantom, such as the ADNI phantom from the Phantom Laboratory, Inc.

In addition to the properties described above, the material of the container 14 may be selected based on other properties such as non-reactivity with compounds within the homogeneous aqueous solution 30, material strength, puncture resistance, fracture resistance, and the ability to be repeatedly autoclaved without significant degradation.

Referring back to FIG. 1, the container 14 includes an opening 32 that functions as a conduit through which the container 14 may be filled with the homogeneous aqueous solution 30. The opening 32 may also be sealed off using any means known in the art such as a stopper, screw cap, a sealed access door, or a cap having an O-ring.

3. Methods of Producing Phantom Calibration Body

Complete dissolution and mixing of the polymers in the homogeneous aqueous solution 30 is a critical process in order to produce the solution 30 suitable for use in the phantom calibration body 12. Conventional methods of producing solutions 30, such as adding a solvent to a measured quantity of polymer until the desired concentration is achieved may not result in complete dissolution of the polymer when used with the high molecular weight polymer species described above. Therefore, the methods used to produce the homogeneous aqueous solution 30 are selected to ensure complete, homogeneous dissolution of the polymers and other additives.

In general, the preparation of homogeneous polymer aqueous solutions 30 from hydrophilic glassy polymers with high solute content are challenging due to inter- and intra-molecular interactions between the polymers such as hydrogen bonding, leading to entanglement of the polymer chains and gelation. The production method may include mixing short-chain low molecular-weight polymers with long-chain high molecular-weight polymers. Surprisingly, the addition of low molecular-weight polymers decreases the intra-molecular association among the high molecular-weight polymer molecules as well as the solubility of the high molecular-weight polymers in the solvent. The resulting homogeneous aqueous solution 30 is homogeneous and achieves a polymer concentration of at least 30% (w/w) as described above.

In an exemplary embodiment, a multi-step process is used to produce the homogeneous aqueous solution 30. An amount of the low molecular weight polymer is added to an amount of water until the desired polymer concentration is achieved, forming a low molecular weight polymer solution. Similarly, an amount of the high molecular weight polymer is added to an amount of water until the desired polymer concentration is achieved, forming a high molecular weight solution. Both the low and high molecular weight solutions are mixed and the polymer is added using methods known in the art such as stirring and agitation.

During the formation of the low and high polymer solutions, techniques known in the art may be used to minimize the introduction of gas bubbles into the solutions during production. The formation of bubbles is particularly problematic in the high molecular weight solution, because the high viscosity of this solution resists the release of bubbles. The polymer may be added very slowly during the formation of the solution and the mixing speed may be limited to speeds at which gas is not introduced into the solvent during mixing. In addition, the solutions may be formed in a reduced pressure environment, in order to increase the size of any bubbles, thereby reducing the relative drag on the bubbles with respect to the buoyant force, hastening the elimination of gas out of the homogeneous aqueous solution 30.

The dissolution times of each solution depends on the molecular weight of the polymer in each solution. For example, a polymer with a molecular weight of 10 kDa will dissolve relatively quickly, and a polymer with a molecular weight of greater than 200 kDa will take several hours to dissolve. In order to reduce the dissolution times, the solutions may be heated to a temperature ranging from about 20° C. to about 95° C.

Once the low and high molecular weight solutions have reached dissolution, the high molecular weight solution may be mixed with the low molecular weight solution to produce the homogeneous aqueous solution 30. Any low molecular weight additives may be mixed into the low molecular weight solution prior to adding the high molecular weight solution. To enhance the rate and effectiveness of the homogenization process, the mixture of the two solutions may be stirred and/or heated to a temperature ranging from about 20° C. to about 95° C.

During the preparation of the homogeneous aqueous solution 30, an amount of ions and/or gadolinium-based diffusion MRI contrast agents may be doped into the low molecular weight solution in order to achieve desired $T_1$ and $T_2^*$ relaxation times for the solution 30. Other additives may be mixed into the low molecular weight solution such as antibacterial agents such as sodium azide, ionic and non-ionic surfactants, DMSO, $T_1$ and $T_2^*$ contrast agents, and $D_2O$. Ionic surfactants may be selected from calcium ions, and EDTA.

The high molecular weight solution may be slowly introduced into the low molecular weight solution while continuously mixing the low molecular weight solution. Because the low molecular weight solution has a lower viscosity relative to the high molecular weight solution, the viscosity of the mixture of the solutions increases gradually, thereby enhancing the kinetics of mixing of the solutions and inhibiting the formation of bubbles in the mixture.

In the various production methods described above, the formation of bubbles may be minimized by the selection of appropriate mixing rates and/or mixing the solutions in a low pressure and/or elevated temperature environments. Solutions 30 containing minimal bubbles produce phantom calibration bodies with minimal signal distortion due to susceptibility effects, which cause spatial inhomogeneity in the static magnetic field that adversely affects the measurement of water diffusivity.

In order to minimize the evaporation of solvent from the homogeneous aqueous solution 30 and/or absorption of atmospheric moisture during production of the homogeneous aqueous solution 30, the solution may be produced within an appropriate closed container. Non-limiting examples of closed containers include laboratory glassware with a stirrer. The polymer solution 30 may also be produced using other equipment known in the art such as pressurizable laboratory reactors, ultrasonic homogenizers, high viscosity mixers and agitators for mixing high viscosity materials.

4. Methods of Using Phantom Calibration Body

The phantom calibration body 12 may be used to calibrate a diffusion MRI device. A method to calibrate a diffusion MRI device may include placing the phantom calibration body 12 in the diffusion MRI device, obtaining measurements of the phantom calibration body 12 by scanning the phantom calibration body 12 with the diffusion MRI device, calculating a measure of water diffusivity including, but not limited to, ADC or diffusion tensor quantities based on imaging data of at least one diffusion MRI image obtained from the diffusion MRI device.

The method for calibration may also include scanning the phantom calibration body 12 using a diffusion-weighted MRI sequence to obtain diffusion-weighted MRI data.

The imaging data obtained from measurements of the phantom calibration body 12 by the diffusion MRI device may be subsequently used to calibrate the diffusion MRI device for consistency throughout the available image volume of the diffusion MRI device, consistency with diffusivity data obtained previously by the same diffusion MRI device, and consistency with diffusivity data obtained using other diffusion MRI devices.

a. Routine Maintenance of Diffusion MRI Devices

The phantom calibration body 12 may be used to calibrate the diffusion MRI device 16 as a maintenance routine by on-site personnel or as a service package from an equipment vendor. The phantom calibration body 12 may be used by equipment vendors, diffusion MRI technicians, or researchers in institutional departments such as the radiology departments of research institutions, laboratories, universities, hospitals, and/or clinics in order to calibrate institutional diffusion MRI devices. The calibrations may be performed as part of routine maintenance procedures and/or to assess the effects of the repair, adjustment, upgrade, or replacement of hardware or software components of the diffusion MRI device on diffusion image quality. In addition, the calibrations may be performed on two or more diffusion MRI devices 16 at the same or different institutions using the same phantom calibration body 12 in order to standardize the quality of the diffusion images for comparative purposes.

b. Quality Assurance and/or Quality Control Processes

The phantom calibration body 12 may be used by vendors of diffusion MRI devices 16 as part of a quality assurance and/or quality control process. The calibration may take place at the diffusion MRI device 16 manufacturing facility prior to shipping the device to a purchaser or after the installation of an diffusion MRI device at the purchaser's facility. In addition, the vendor may perform a calibration as part of a diagnostic process prior to the repair of a malfunctioning diffusion MRI device, and/or to determine whether a repair procedure performed on the device was successful. The vendor may perform a periodic calibration of all diffusion MRI devices produced by the manufacturer currently in use to ensure consistent diffusion image quality among all diffusion MRI devices. The vendor may perform a calibration of a diffusion MRI device according to standard or proprietary protocols as part of a quality assurance (QA) and quality control (QC) program.

c. Manufacturing or Development Processes

The phantom calibration body 12 may be used to calibrate the diffusion MRI device 16 at a manufacturing facility in order to assess the quality of the diffusion image produced by a particular manufacturing process. In this case, the results of the calibration may be used as a measure of quality and reproducibility of the manufacturing process.

Alternatively, the phantom calibration body 12 may be used to calibrate a prototype diffusion MRI device at a manufacturing facility. In this case, the results of the calibration may be used as a measure of the quality of the design, or the results of the calibration may provide information used to refine the design of the prototype diffusion MRI device.

d. Diffusion MRI Resolution Calibration

As described previously, the phantom calibration body 12 may include a container 14 of known dimension. The dimensions of an diffusion MRI image obtained using the phantom calibration body 12 may be compared to the known dimensions of the container 14 in order to assess various aspects of the image quality such as image spatial resolution and image distortion.

e. Diffusion MRI Calibration System

Figure 2:
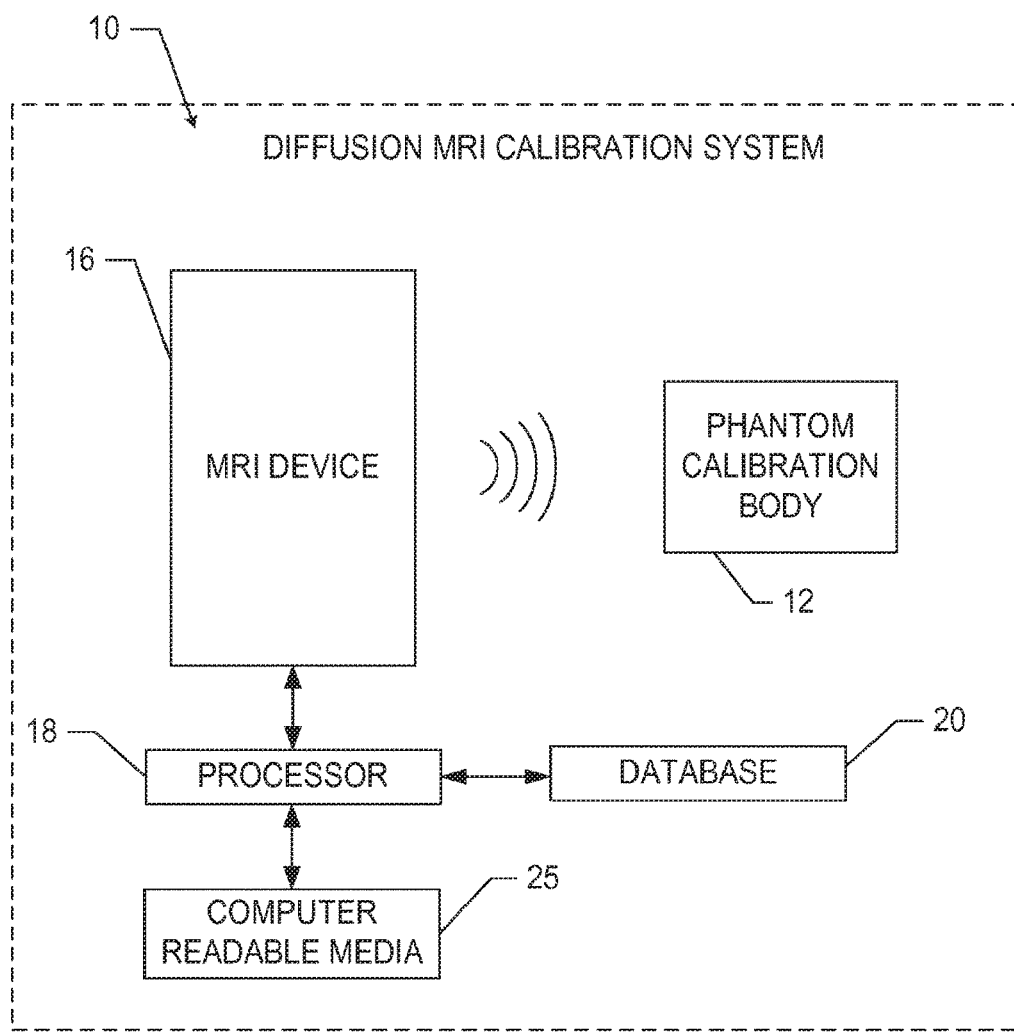
FIG. 2 is a simplified block diagram of a diffusion MRI calibration system for calibrating a diffusion MRI device using a phantom calibration body.

Referring to the drawings, an embodiment of a diffusion MRI calibration system is illustrated and generally indicated as 10 in FIG. 2. The diffusion MRI calibration system 10 may be used to calibrate a diffusion MRI device 16 using a phantom calibration body 12.

Embodiments of the diffusion MRI calibration system 10 include particular components for providing various functions as discussed above. The diffusion MRI device 16 may be controlled using one or more processors 18 embodied in one or more distributed or integrated component or systems that store data, such as imaging data of the phantom calibration body 12. The diffusion MRI calibration system 10 further includes a database 20 on which data is stored on a computer readable media 25 on which one or more algorithms, software, modules, data, computer-readable instructions, and/or firmware may be loaded and/or operated and/or which may operate on one or more processors 18 to implement the systems and methods identified herein. In an embodiment, the database 20 may be a storage system that temporarily and/or permanently stores image data and may include volatile and/or nonvolatile memory and/or other types of storage systems or devices. The computer readable media 25 may include volatile media, nonvolatile media, removable media, non-removable media, and/or other media or mediums that can be accessed by a general purpose or special purpose computing device. For example, computer readable media 25 may include computer storage media and communication media, including computer readable media. Computer storage media may further include volatile, non-volatile, removable, and/or non-removable media implemented in a method or technology for storage of information including, but not limited to, computer readable instructions, data structures, program modules, and/or other data. Communication media may, for example, embody computer readable instructions, data structures, program modules, algorithms, and/or other data. The communication media may include wired and/or wireless connections and technologies and may be used to transmit and/or receive wired or wireless communications. Combinations and/or subcombinations of the systems, components, modules, and methods and processes described herein may be made.

f. Diffusion Tensor MRI (DTI) System

The phantom calibration body 12 may be used as an isotropic phantom body 12 for the measurement of isotropic diffusivity. The measurement of a "standard" isotropic diffusivity is an important method for calibrating a scalar diffusion constant or ADC for the MRI device 16. However, it is not known in the art that such a measurement of the isotropic diffusivity has utility in calibrating methods for the MRI device 16 to characterize more complex modes of diffusion, such as anisotropic diffusion, that requires a description using a second rank diffusion tensor, or a non-Gaussian diffusion, that requires even higher order mathematical objects. For example, one of the most stringent tests of a DTI measurement is that the estimated or measured diffusion tensor in each voxel within a homogeneous isotropic medium is an isotropic tensor having the correct value of the trace or mean ADC. Aberrations or artifacts in the MRI gradient or radio frequency (RF) receiver or transmitter hardware, MRI sequences used to obtain the diffusion-weighted images (DWIs), image reconstruction software used to obtain raw DWI data, and post processing algorithms applied to these DWIs may all introduce errors that may cause the measured diffusion tensors to deviate from their correct isotropic form. As such, the spatial uniformity or homogeneity of the measured isotropic diffusion tensors within an isotropic homogeneous phantom calibration body 12 is a powerful benchmark for validating the DTI acquisition, processing and analysis processes.

In higher order diffusion MRI applications that attempt to discover finer orientational features or the angular dependence of the displacement distribution, such as Q-ball MRI, an isotropic phantom body 12 may be used to assess whether any artifactual systematic orientational biases are introduced into the measurements, or to assess the susceptibility of the measurement signals to noise. In displacement MRI methods that involve measuring the diffusion-weighted image signal decay as a function of the length scale being probed, an isotropic phantom may be used to ensure that for all length scales for which the diffusion process is Gaussian and isotropic, the correct diffusion properties are determined. This method has particular applications for single and multiple pulsed field gradient (PFG) MRI methods, such as single and double PFG MRI methods.

The isotropic phantom calibration body 12 may be used to calibrate any diffusion MRI methods that utilize diffusion-weighted images (DWI) or data to obtain a finding or result. These calibration methods include, but are not limited to, diffusion tensor MRI (DTI or DT-MRI), diffusion spectrum imaging (DSI), Q-ball imaging (QBI), composite hindered and restricted model of diffusion (CHARMED) MRI, AxCaliber MRI, spherical harmonic operator representation (SHORE) MRI, single pulsed-field gradient (PRG), double and multiple PRG MRI, and functional diffusion MRI (fDI).

g. Combined Diffusion MRI/Resolution Phantom Calibration Body

The phantom calibration body 12 may be used as a combined diffusion MRI/resolution phantom calibration body. In this method of use, the same phantom calibration body 12 may be used to calibrate an MRI device's image quality as well as the accuracy and precision of the MRI device's diffusion measurements. This use may be particularly desirable for implementing QA processes in Radiological departments and for assuring data quality in longitudinal and multi-subject studies using measurements obtained using an MRI device.

5. Exemplary Embodiments of Phantom Calibration Body

Exemplary embodiments of the phantom calibration body 12 are presented below.

a. Brain Tissue Phantom

In one exemplary embodiment, the homogeneous aqueous solution 30 of the phantom calibration body 12 may have water diffusivity properties that effectively simulate those of brain tissue. Brain tissue is a challenging tissue to mimic using a phantom calibration body 12, due to the large proportions of membrane space, fibers, and micro-structures of the brain, as well as the small proportion of free space relative to other tissues of the body. In this embodiment, the phantom calibration body 12 includes a homogeneous aqueous solution 30 that includes about a 65% (w/w) concentration of polymers, and has a measured ADC of about of $3 \times 10^{-4}$ mm$^2$/s at room temperature, which is essentially similar to the ADC measured in gray matter, and the ADC measured perpendicular to brain white matter fibers. Persons of skill in the art may vary the polymer mixture concentration and/or mixing ratio of the constituent components to obtain water diffusivity characteristics that essentially match those of other tissues as discussed herein.

b. Multi-Chambered Phantom Calibration Body

Figure 3A:
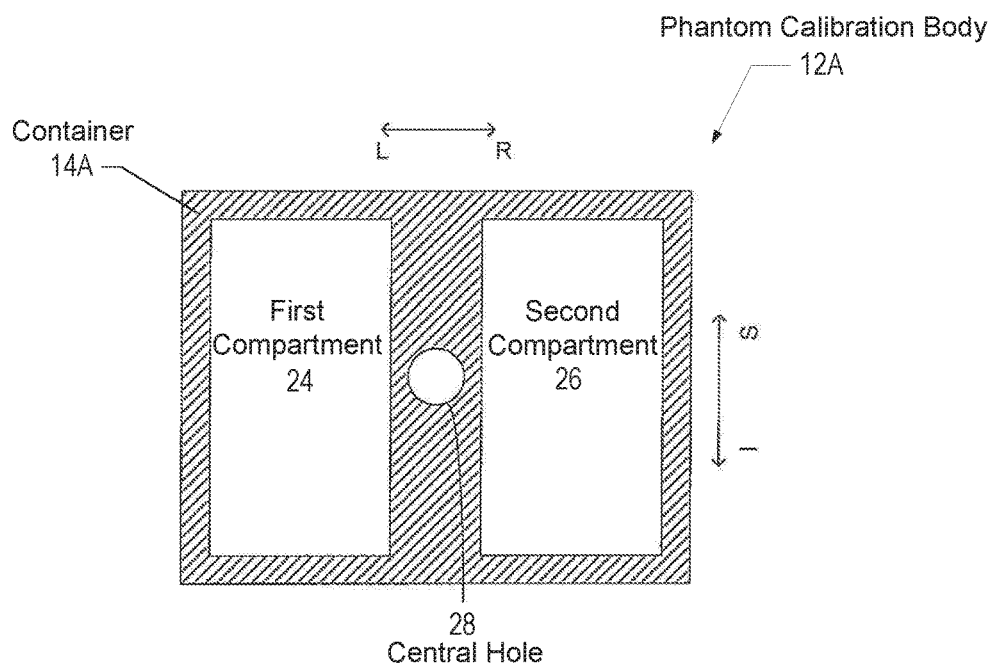
FIG. 3A is an front view illustrating an embodiment of the phantom calibration body.
Figure 3B:
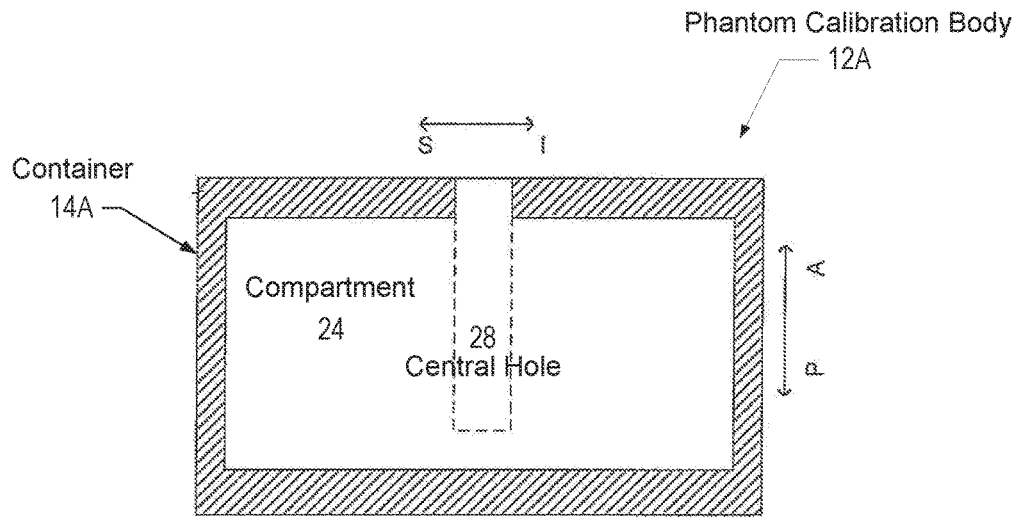
FIG. 3B is a side view illustrating embodiment of the phantom calibration body.
Figure 3C:
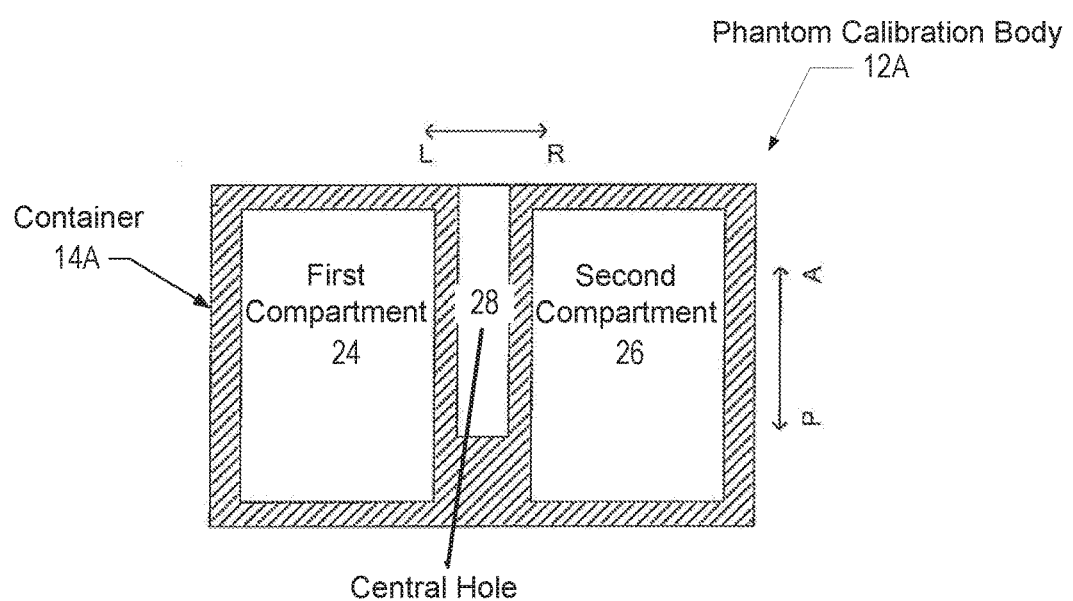
FIG. 3C is a top view illustrating embodiment of the phantom calibration body.

FIGS. 3A-3C show the front view, side view, and top view respectively of one embodiment of a multi-chambered phantom calibration body 12A. In this embodiment, the phantom calibration body 12A includes a container 14A that defines a first compartment 24, a second compartment 26, and a central hole 28. First and second compartments 24 and 26 contain aqueous solutions of mixtures of polymers at varying concentrations of at least 1% (w/w) of the mixture. The central hole 28 acts as a reference compartment for housing a second solution that may include, but is not limited to, a saline sample. The second solution acts as a reference with respect to diffusivity having a diffusion coefficient in sharp contrast to those of the solutions in the first and second compartments 24 and 26. Container 14A may further include a cap with an O-ring (not shown) for sealing off compartments 24 and 26.

EXAMPLES

The following examples illustrate various aspects of the embodiments that may be implemented by the diffusion MRI calibration system 10.

Example 1: Production of Phantom Calibration Body

To demonstrate the feasibility of forming highly concentrated homogeneous solutions containing mixtures of low molecular-weight and high molecular-weight polymers for manufacturing the phantom calibration body 12, the following experiment was conducted.

Solutions of PVP (Sigma-Aldrich) ranging from 15% to 65% w/w were prepared in either pure water or saline solution (0.9% w/w). Polymer solutions were prepared in three-necked round flasks of 1000 ml in volume provided with a stirrer, a reflux cooler, and a thermometer as well as with an electric heating jacket. For example, a 47% PVP solution was achieved by weighing about 220 g of the high molecular weight poly(vinyl pyrrolidone) (average molecular weight 75 kDa) previously dried at 102° C. for 6 hours and dissolved in about 280 ml deionized water in a 1000 ml round flask at 85° C. The resistivity of the deionized pure water used in this process was about 18.2 megohm as obtained from Millipore's Reagent Grade water purification system. All 15 to 65% PVP solutions were heated and stirred at 85° C. until the polymer was completely dissolved. For the 47% PVP solution, about 70 g of the low molecular weigh dry poly(vinyl pyrrolidone) sample (average molecular weight 15 kDa) was separately weighed and used. The low molecular weight dry poly vinyl pyrrolidone had been previously dried at 106° C. for 4 hours and dissolved in 50 ml deionized water (resistivity: 18.2 megohm) in a 1000 ml round flask at 85° C. Again, during the dissolution step, stirring was applied. To the low molecular weight polymer solution, the above solution of the high molecular weight polymer was added while the flask was agitated. There was no temperature change during the mixing process. After completion of the addition of the high molecular weight polymer solution, the temperature was raised to 95° C. by external heating. The mixture was kept at 95° C. to expel suspended air bubbles. While the internal temperature was maintained, stirring was continued as a solution of 0.05 g sodium-azide in 1.0 ml water was added as a preservative. Stirring was continued for 4 hours before cooling to 25° C.

For all PVP solutions, the concentration of the solid content was measured after cooling. A gravimetric method was used, in which the solvent (water) was evaporated and the sample weight was measured until a constant value was obtained. This method required a high precision scale and 1-2 milliliter sample volumes. The solvent evaporation took place at 100° C. at atmospheric pressure for several hours (overnight). The concentration was expressed in weight fraction (or weight percent, wt %)

$$wt\ \% = 100 \frac{w_2}{w_1 + w_2}$$

where w1=grams of solvent (water) and w2=grams of solute (polymer+salts). In the present example the concentration of the solution was 46.9 wt %.

The results of this experiment demonstrated the feasibility of forming highly concentrated homogeneous solutions containing mixtures of low molecular-weight and high molecular-weight polymers for manufacturing the phantom calibration body 12

Example 2: Effect of Temperature on ADC of Phantom Calibration Body

To assess the water diffusion properties of a prototype phantom calibration body 12, and to further assess the sensitivity of the water diffusion properties to changes in temperature, the following experiment was conducted.

A phantom calibration body 12 with a 65% polymer mixture content (w/w) was produced using the methods described in Example 1. The polymers in the phantom calibration body 12 included 10% low molecular-weight PVP (molecular weight of about 10,000 Da) and 90% of a high molecular-weight PVP (molecular weight of about 40,000 Da). Diffusion MRI data was obtained from the phantom calibration body 12 at 20.6° C. (room temperature) and 37° C. (physiological temperature). Diffusion data was acquired with single-shot echo planar imaging (EPI) sequences and involved a total of 120 different gradient direction h-values, with a maximum b of 1100 s/mm². The measurements were conducted using a General Electric (GE) 3T Excite scanner with 40 mT/m maximum gradient strength and a Nova 16 Channel coil.

Figure 4:
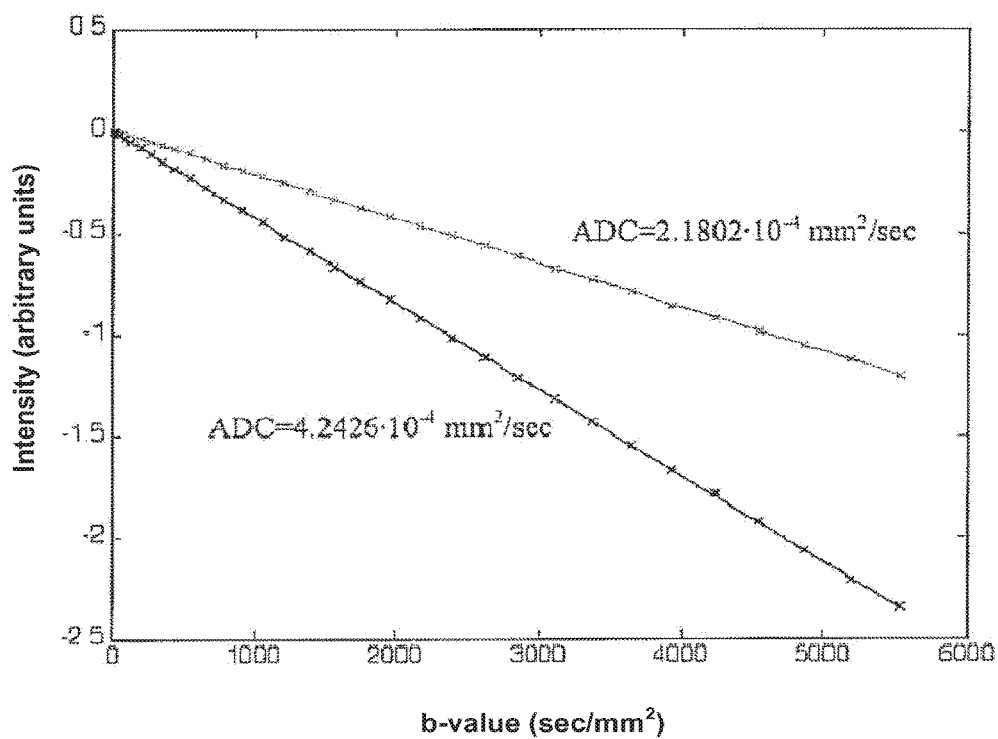
FIG. 4 is a graph showing measured log signal intensities as a function of b-value for a 65% (w|w) polymer phantom calibration body at 20.6° C. (upper line) and at 37° C. (lower line)

FIG. 4 summarizes the measured signal intensity as a function of b-values for the phantom calibration body 12 at 20.6° C. (upper line) and at 37° C. (lower line). The ADC was determined from the slopes of the two lines shown in FIG. 4. The ADC of a pure water sample was determined using the same method described above. Table 1 summarizes the ADC values determined from the water sample and the phantom calibration body:

TABLE 1

COMPARISON OF ADC FOR PHANTOM BODY VS. WATER

| | ADC (mm²/sec) | |
| --- | --- | --- |
| Temperature (° C.) | Phantom Body (65% polymer solution) | Pure Water (0% polymer solution) |
| 20.6 | $2.18 \times 10^{-4}$ | $2.02 \times 10^{-3}$ |
| 37 | $4.24 \times 10^{-4}$ | $2.99 \times 10^{-3}$ |

The ADC values for pure water were larger than those of the phantom calibration body 12 and may be due to free water molecules in pure water having more mobility than those in the copolymer solution, as expected. The measured ADC values for pure water were also consistent with previously published values.

The results of this experiment demonstrated that the 65% concentration of a copolymer solution had a water diffusivity, measured by ADC, comparable to that of human tissues. Specifically, for aqueous solutions of polymers and/or copolymers, the diffusivity of water molecules measured by ADC may be varied over a broad range from about $3 \times 10^{-3}$ mm²/s, which is about the diffusivity of pure water, to about $2 \times 10^{-4}$ mm²/s, which is lower than the diffusivity of water molecules in virtually any biological tissue at 37° C.

Example 3: Effect of Polymer Concentration on Diffusion Characteristics of Phantom Calibration Body To determine the effects of the polymer concentration on the diffusion characteristics of water within a phantom calibration body 12 containing mixtures of low molecular weight and high molecular weight polymers, the following experiment was conducted.

A series of phantom calibration bodies 12 having PVP concentrations ranging from 15% to 71% as described in Example 1 were obtained. ADC measurements were obtained at a temperature of 22° C. for each PVP solution using the methods described in Example 2.

MRI data was acquired using a GE 3T Excite scanner with 40 mT/m maximum gradient strength and a Nova 16 Channel coil at 22° C. Diffusion data was acquired using a single-shot EPI and consisted of 120 different gradient direction/b-values, with a maximum value of b=1100 s/mm². $T_1$ relaxometry was performed with a DESPOT (3) acquisition (TR=8.1 ms, four flip angles=30, 19, 10 and 2 degrees, B1 mapping with 150, 450, and 750 ms inversion recovery acquisitions). $T_2$ relaxometry was performed with a spin echo acquisition (TE ranging from 10 to 700 ms). Additional NMR data was acquired in a 47% PVP solution on a Bruker 7T vertical spectrometer with 1000 mT/m maximum gradient strength and a temperature controlled probe set to 20.6° C. The experiments under this example were aimed at evaluating the mono-exponentiality of the signal decay at b-values up to 6,000 s/mm² and the effect of varying the diffusion time (Δ) from 20 to 200 ms.

Figure 5:
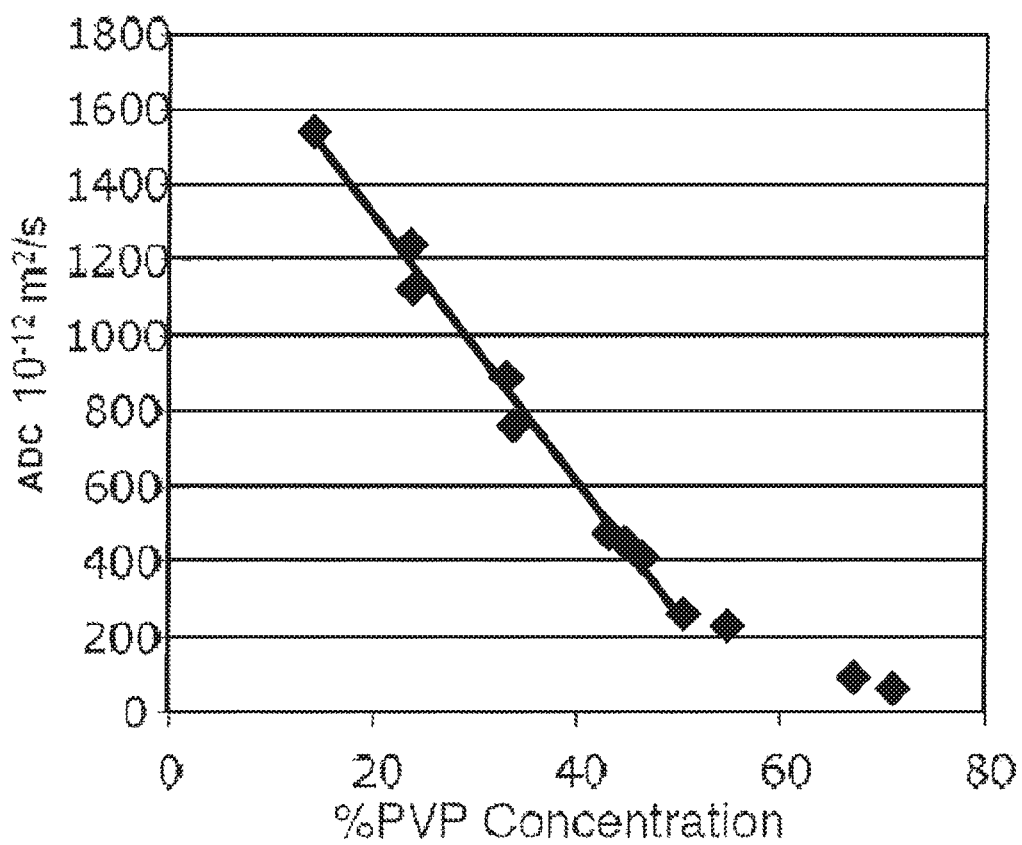
FIG. 5 is a graph showing the results of measured apparent diffusion coefficient (ADC) as a function of the concentration of polyvinyl pyrrolidone (PVP) solution in the phantom calibration body.

The ADC measurements are summarized in FIG. 5 as a function of PVP concentration. The measured ADC values were linearly correlated ($R^2$=0.992) to the PVP mixture concentration up to a concentration of 50%, with a slope of −35.4 and an intercept with the vertical axis at $2025 \times 10^{-12}$ mm²/s. The intercept ADC value, representing the ADC at a polymer concentration of 0%, was very close to the documented ADC of free water at 22° C. At higher PVP concentrations, the relationship between ADC and PVP concentration diverted from linearity and exhibited more complex behavior.

Figure 6:
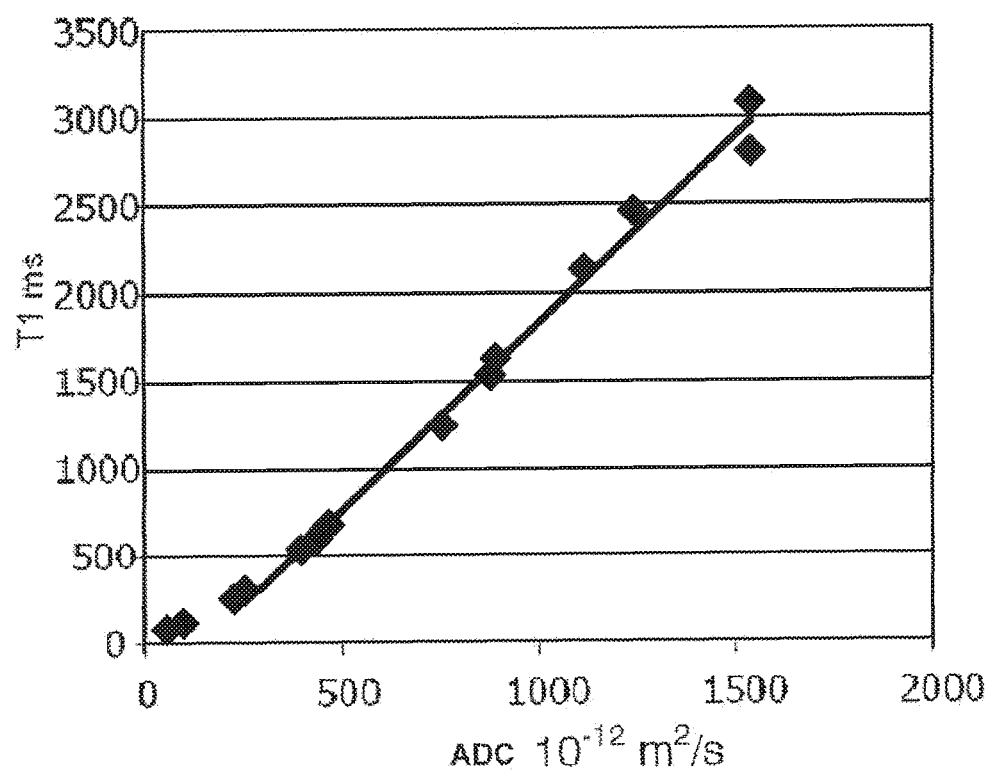
FIG. 6 is a graph showing the relaxation time $T_1$ as a function of measured ADC in the phantom calibration body.

In addition, the relaxation time $T_1$ of each polymer concentration was measured from the diffusion MRI data used to determine the ADC. FIG. 6 summarizes the relaxation times $T_1$ as a function of the measured ADC for each polymer solution. Based on FIG. 6, an ADC of $8.0 \times 10^{-4}$ mm²/s, typical of gray matter in the human brain, corresponded to a $T_1$ of 1392 ms, which was slightly higher than the previously reported $T_1$ of brain tissue at 3 T. Furthermore, the measured $T_2$* of the PVP mixture solution was generally higher than that of brain tissue. For example, a $T_2$* of 196 ms was measured at 55% PVP mixture concentration.

The results of this experiment demonstrated that a homogeneous aqueous solution that included PVP polymer possessed a range of water diffusivity values that included the range of diffusivities representative of known tissues including grey matter, such as brain tissue. In particular, a PVP concentration of about 50% possessed diffusion characteristics that were essentially the same as many tissues. However, the $T_1$ and the $T_2^*$ relaxivity characteristics of the polymer solutions were typically higher than the relaxivity of tissues having essentially the same diffusivity.

Example 4: Effect of Diffusion Time on Diffusion Characteristics of Phantom Calibration Body To characterize the diffusion characteristics of water within the phantom calibration body 12 containing mixtures of lower molecular weight and higher molecular weight polymers, the following experiment was conducted.

A 47% PVP mixture solution obtained using the methods described in Example 1 was placed in a Bruker 7T vertical spectrometer with 1000 mT/m maximum gradient strength and a temperature-controlled probe set to 20.6° C. Measurements were conducted at b-values of up to 6000 s/mm² and for diffusion times ranging from 20 ms to 200 ms.

Table 2 summarizes the measured ADC of the 47% PVP mixture solution as a function of diffusion time Δ. Up to the maximum diffusion time Δ of 200 ms, corresponding to a b-value of 6000 s/mm², the measured ADC appeared to be independent of the diffusion time Δ.

TABLE 2

EFFECT OF Diffusion TIME ON ADC

| Diffusion Time Δ (ms) | ADC ($10^{-4}$ mm²/s) |
|---|---|
| 20 | 3.790 |
| 60 | 3.715 |
| 120 | 3.705 |
| 200 | 3.691 |

The results of this experiment indicated a Gaussian diffusion of a single population of spins for the polymer solution tested. This characteristic is a desirable feature in a diffusion phantom body to be used for calibration purposes.

Example 5: Stability of Polymer Solution in Phantom Calibration Body

To characterize the stability over time of the phantom calibration body 12 containing mixtures of lower molecular weight and higher molecular weight polymers, the following experiment was conducted.

A 43% PVP mixture solution produced using the methods described in Example 1 were stored in a sealed container and scanned three times over a period of 15 months. The variation of measured ADC over that period was determined to be about 2%.

The results of this experiment indicated that the 43% PVP mixture solution was stable for a period of at least 15 months.

Example 6: Isotropic Diffusion in Phantom Calibration Body

To characterize the isotropic diffusion characteristics of water within the phantom calibration body 12 containing mixtures of lower molecular weight and higher molecular weight polymers, the following experiment was conducted.

A series of diffusion MRI measurements were conducted on four phantom calibration bodies 12 using methods similar to those described in Example 4. Each phantom calibration body 12 had a PVP polymer concentration of 0%, 24.3%, 34.5%, and 46.6%, respectively. For each phantom calibration body 12, each measurement in the series of diffusion MRI measurements varied the b-value through a range of different values.

Figure 7:
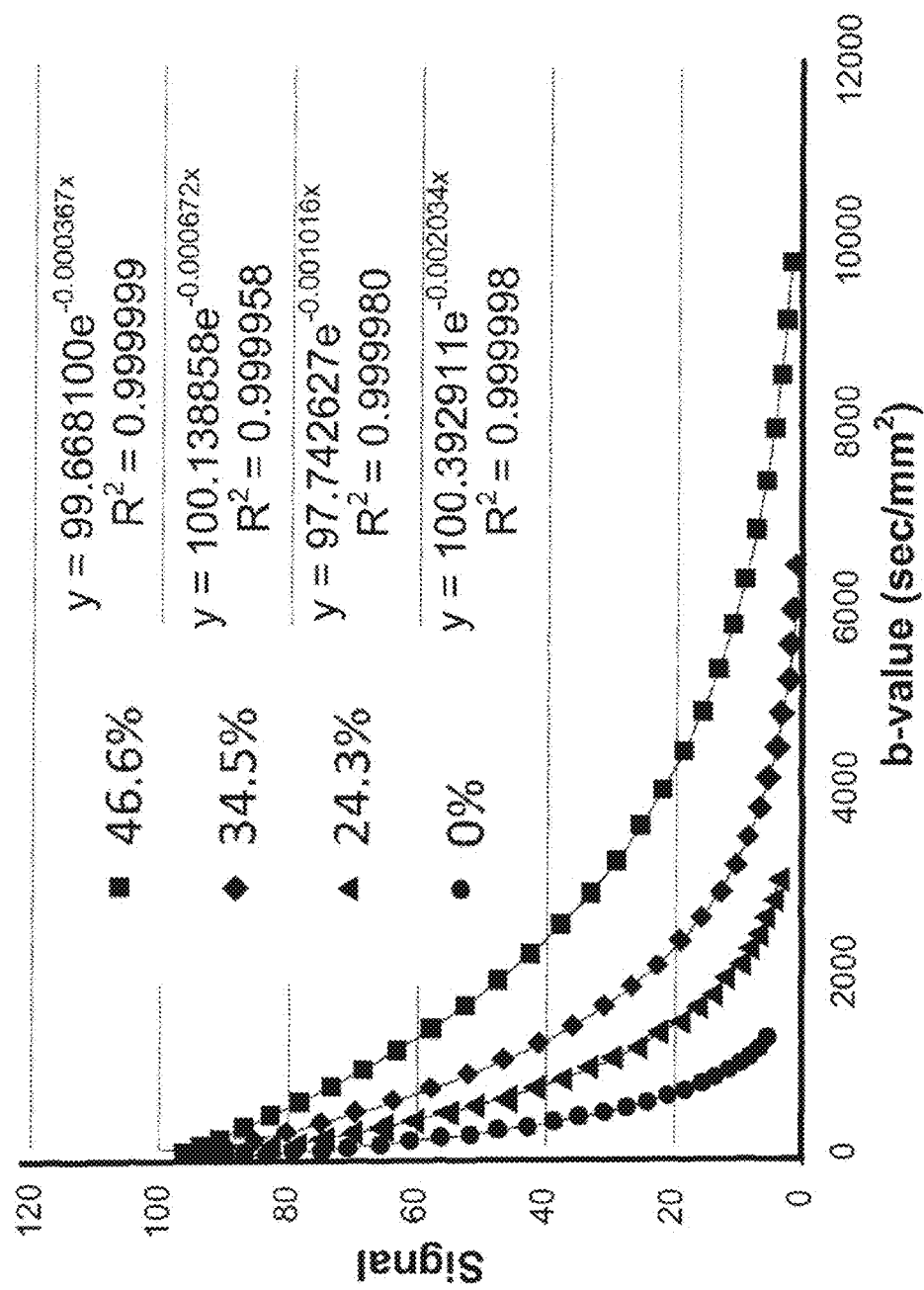
FIG. 7 is a graph showing the monoexponential decay of an MRI signal vs. b-value at different PVP concentrations.

The results of these measurements are summarized in FIG. 7. At each PVP concentration, the MRI signal decayed exponentially with increasing b values. The curve fits, also shown in FIG. 7, each had $R^2$ values very near to unity for all concentrations, indicating that a monoexponential diffusion model fits the data perfectly. The monoexponential diffusion model is consistent with isotropic diffusion characteristics.

The results of this experiment indicated that the phantom calibration body 12 has isotropic diffusion properties throughout a range of polymer concentrations.

Example 7: Effects of Temperature and Polymer Concentration on Diffusion in Phantom Calibration Body To characterize the effects of temperature on the diffusion characteristics of water within of the phantom calibration body 12 containing various mixtures of lower molecular weight and higher molecular weight polymers, the following experiment was conducted.

A series of diffusion MRI measurements were conducted on four phantom calibration bodies 12 similar to those described in Example 6 using methods similar to those described in Example 4. Within the series of measurements for each phantom calibration body 12, the temperature was varied from about 20° C. to about 37° C.

Figure 8:
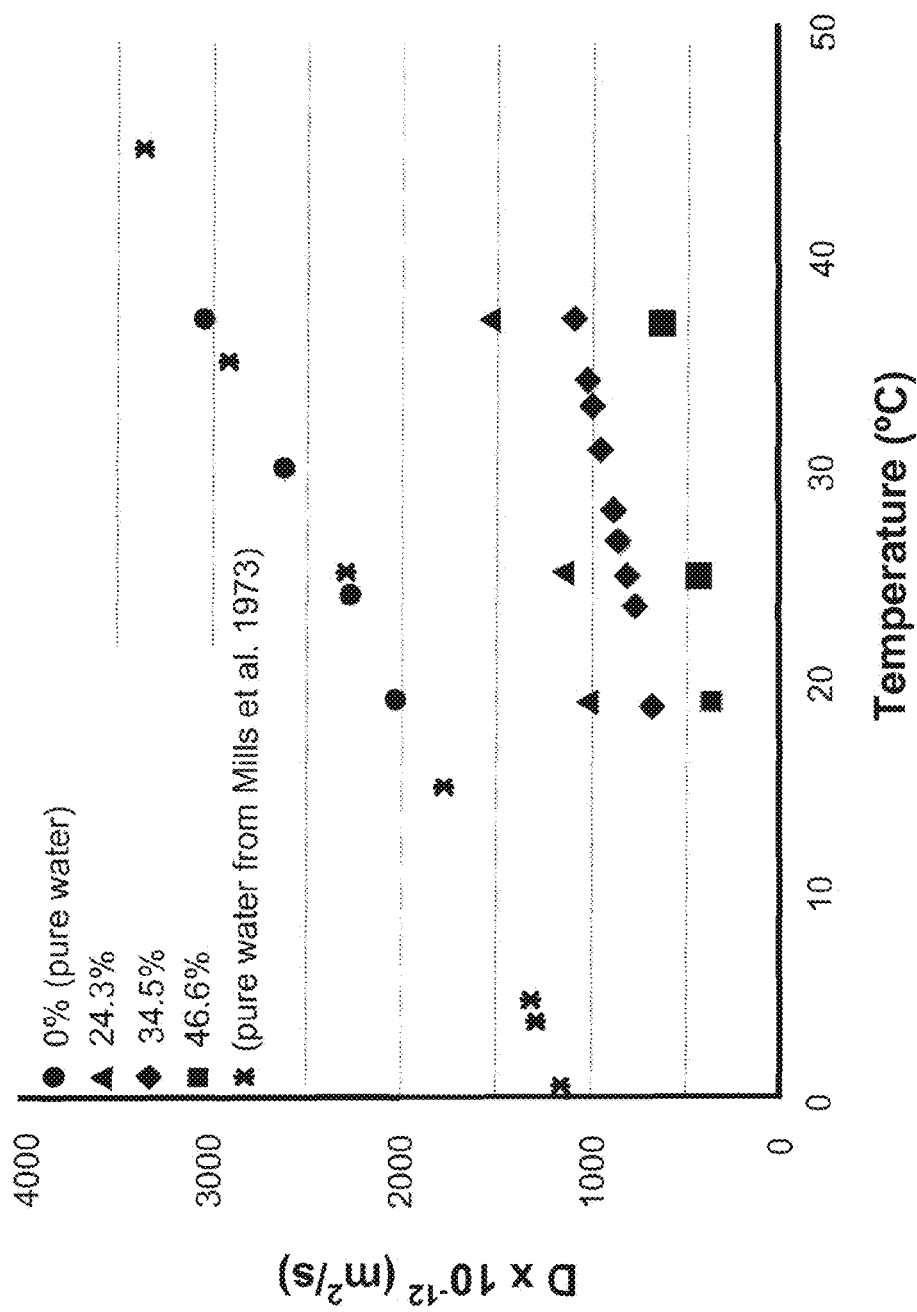
FIG. 8 is a graph showing the measured ADC as a function of temperature and PVP concentrations.

The results of this experiment are summarized in FIG. 8, which shows the measured apparent diffusion coefficient (ADC) as a function of temperature and PVP polymer concentration. The pure water (0% polymer concentration) ADC values are consistent with previously published data (Mills et al 1973). In general, measured ADC values decrease as polymer concentration increases, and as temperature decreases. Interestingly, the measured ADC values of the polymer solutions at room temperature obtained ADC values that were well below the ADC value of pure water at 0° C.

The results of this experiment demonstrated that the polymer solutions of the phantom calibration body 12 achieved a range of diffusivity values that are well-suited to mimic the large range of diffusivity characteristics found in biological tissues.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A system that performs diffusion magnetic resonance imaging (MRI), comprising: a phantom calibration body comprising:

a homogenous aqueous solution of polyvinyl pyrrolidone having a distribution of molecular weights with a mean of 5-1000 kilo Daltons (kDa);

the homogenous aqueous solution having a diffusivity that is essentially the same as a target mammalian tissue and a viscosity ranging from about $10^2$ centistokes (cSt) to about $10^6$ cSt; and, a diffusion MRI device configured for scanning the phantom calibration body in order to generate diffusion imaging data of the phantom calibration body, wherein the MRI device comprises one or more processors and wherein the diffusion imaging data are provided and stored on at least one of the one or more processors.

2. The system of claim 1, wherein the homogeneous aqueous solution comprises at least 0.1% (w/w) polyvinyl pyrrolidone.

3. The system of claim 1, wherein the homogeneous aqueous solution comprises 1% to 80% (w/w) polyvinyl pyrrolidone.

4. The system of claim 1, wherein the homogeneous aqueous solution comprises 5% to 20% (w/w) polyvinyl pyrrolidone.

5. The system of claim 1, wherein the homogeneous aqueous solution comprises 20% to 80% (w/w) polyvinyl pyrrolidone.

6. The system of claim 1, wherein the distribution of molecular weights has a mean of 5 to 40 kDa.

7. The system of claim 1, wherein the distribution of molecular weights has a mean of 40-1000 kDa.

8. A method of diffusion MRI, comprising:
providing the system of claim 1;
placing the phantom calibration body of claim 1 into the diffusion MRI device of claim 1;
obtaining diffusion imaging data of the phantom calibration body by scanning the phantom calibration body with the diffusion MRI device; and
calculating a diffusivity measurement based on the diffusion imaging data that is indicative of water diffusivity of the homogeneous aqueous solution,
wherein the diffusivity measurement is calculated and provided back into the MRI device as a result by at least one of the one or more processors.

9. The method of claim 8, wherein the diffusion MRI is performed in order to calibrate the diffusion MRI device.

10. The method of claim 9, wherein the calibration is performed as part of an activity selected from the group consisting of:
a routine maintenance of the diffusion MRI device,
a troubleshooting and repair process on the diffusion MRI device,
a quality assurance/quality control process on the diffusion MRI device, and
a performance assessment of a prototype diffusion MRI device in a design process.

11. A method of diffusion magnetic resonance imaging (MRI), comprising:
providing a phantom calibration body comprising:
a homogenous aqueous solution of polyvinyl pyrrolidone having a distribution of molecular weights with a mean of 5-1000 kilo Daltons (kDa);
the homogenous aqueous solution having a diffusivity that is essentially the same as a target mammalian tissue and a viscosity ranging from about $10^2$ centistokes (cSt) to about $10^6$ cSt;
placing the phantom calibration body in a diffusion MRI device;
obtaining diffusion imaging data of the phantom calibration body by scanning the phantom calibration body with the diffusion MRI device,
wherein the MRI device comprises:
one or more processors and
wherein the diffusion imaging data are stored on at least one of the one or more processors; and
calculating a diffusivity measurement based on the diffusion imaging data that is indicative of water diffusivity of the homogeneous aqueous solution,
wherein the diffusivity measurement is calculated and provided back into the MRI device as a result by at least one of the one or more processors.

12. The method of claim 11, wherein the diffusion MRI is performed in order to calibrate the diffusion MRI device.

13. The method of claim 12, wherein the calibration is performed as part of an activity selected from the group consisting of:
a routine maintenance of the diffusion MRI device,
a troubleshooting and repair process on the diffusion MRI device,
a quality assurance/quality control process on the diffusion MRI device, and
a performance assessment of a prototype diffusion MRI device in a design process.

14. The method of claim 11, wherein the homogeneous aqueous solution comprises at least 0.1% (w/w) polyvinyl pyrrolidone.

15. The method of claim 11, wherein the homogeneous aqueous solution comprises 1% to 80% (w/w) polyvinyl pyrrolidone.

16. The method of claim 11, wherein the homogeneous aqueous solution comprises 5% to 20% (w/w) polyvinyl pyrrolidone.

17. The method of claim 11, wherein the homogeneous aqueous solution comprises 20% to 80% (w/w) polyvinyl pyrrolidone.

18. The method of claim 11, wherein the distribution of molecular weights has a mean of 5 to 40 kDa.

19. The method of claim 11, wherein the distribution of molecular weights has a mean of 40-1000 kDa.

* * * * *